United States Patent [19]

Wehrmeister

[11] 3,953,432
[45] Apr. 27, 1976

[54] TRANQUILIZERS

[75] Inventor: Herbert L. Wehrmeister, Terre Haute, Ind.

[73] Assignee: Commercial Solvents Corporation, Terre Haute, Ind.

[22] Filed: Dec. 4, 1972

[21] Appl. No.: 312,242

[52] U.S. Cl. ............... 260/240 E; 260/244 R; 260/307 F; 424/248; 424/272
[51] Int. Cl.² ............ C07D 263/14; C07D 265/08
[58] Field of Search ............... 260/307, 244, 240

[56] References Cited
UNITED STATES PATENTS

| 2,579,478 | 12/1951 | Djerassi et al. | 260/307 |
| 3,466,308 | 9/1969 | Wehrmeister | 260/307 |
| 3,483,141 | 12/1969 | Litt et al. | 260/244 |
| 3,532,645 | 10/1970 | Schulze et al. | 260/307 |
| 3,637,707 | 1/1972 | Koch | 260/240 D |
| 3,681,333 | 8/1972 | Litt et al. | 260/244 |
| 3,682,948 | 8/1972 | Tomalia et al. | 260/244 |
| 3,778,445 | 12/1973 | Timmons et al. | 260/307 F |
| 3,901,906 | 8/1975 | Kozlik | 260/307 F |

OTHER PUBLICATIONS

Nordin, J. Heterocyclic Chem., Vol. 3, p. 531–532 (1966).
Seeliger, Angew Chem. Internat'l Engl. Ed., Vol. 5, p. 887 (1966).

Primary Examiner—Harry I. Moatz
Attorney, Agent, or Firm—Robert H. Dewey; Howard E. Post

[57] ABSTRACT

Tranquilizing agents for warm-blooded animals corresponding to the formula

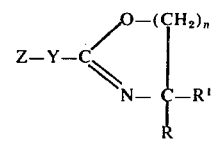

where $n$ can be 1 or 2; Y can be

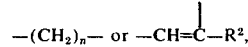

where $R^2$ can be hydrogen or an alkyl, alkenyl, alkoxy, phenyl or methoxyphenyl radical. Z can be thienyl, furyl, phenyl; or mono-, di-, or trimethoxyphenyl; mono-, or dichlorophenyl, or dichlorophenoxy. R and $R^1$ can be hydrogen, methyl, or ethyl and can be the same or different.

8 Claims, No Drawings

TRANQUILIZERS

BACKGROUND OF THE INVENTION

This invention relates to tranquilizing agents for warm-blooded animals. In a particular aspect, this invention relates to certain oxazines and oxazolines useful as tranquilizing agents.

Tranquilizing agents are very useful in calming animals. For example, they are very helpful treating sick animals and in the capture and transportation of wild animals. Many tranquilizing agents are known, among which are oxazolines of the formula

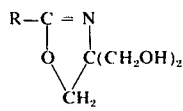

where R is halogenyl phenyl, o-hydroxyphenyl or m-trifluoromethyl, as disclosed by L. F. Wiggins et al., U.S. Pat. No. 3,235,557.

SUMMARY OF THE INVENTION

It is an object of this invention to provide a method for tranquilizing warm-blooded animals.

It is another object of this invention to provide tranquilizing agents of the class of oxazines and oxazolines.

Other objects of this invention will be apparent to those skilled in the art from the disclosure herein.

It is the discovery of this invention that compounds represented by the formula

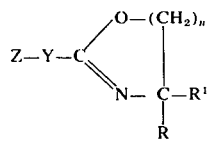

are central nervous system depressants which are useful in the calming of animals. In the formula, $n$ can be 1 or 2; Y can be the group $-(CH_2)_n-$, where $n$ is 1 or 2, or

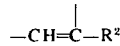

where $R^2$ can be hydrogen, or an alkyl, alkenyl, or alkoxy group of from 1 to 8 carbon atoms, or $R^2$ can be phenyl or methoxyphenyl.

Z can be thienyl, furyl, phenyl; or Z can be mono-, di- or trimethoxyphenyl; mono- or dichlorophenyl, or dichlorophenoxy. R and $R^1$ can be hydrogen, methyl, or ethyl, and can be the same or different.

DETAILED DISCUSSION

The oxazolines suitable for the practice of this invention can be readily prepared from alkanolamines corresponding to the formula:

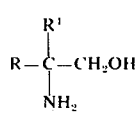

where R and $R^1$ have the same meaning as set forth hereinbefore, and a suitable acid. When Y is $-CH=CH-$, the acid is acetic acid; and when Y is

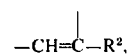

the acid is an alkyl or alkenyl acid corresponding to the formula $R^2CH_2COOH$. When Y is $-(CH_2)_n-$, a suitable acid is phenyl alkanoic or substituted phenyl alkanoic acid. These oxazolines are prepared by known methods, e.g., the method of Purcell, U.S. Pat. No. 3,336,145, which is incorporated herein by reference. When Y is

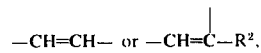

Z is provided by condensing the oxazoline with the appopriate aldehyde, e.g., benzaldehyde or substituted benzaldehyde by known methods, e.g., by the method of H. L. Wehrmeister, *J. Org. Chem.* 27, 4418 (1962).

The compounds of the present invention have been found to exert a depressant action on the central nervous system when tested under standard and accepted pharmacological procedures, in animals, such as mice and rats. They are, therefore, deemed to possess utility in experimental and comparative pharmacology and are of value to treat conditions in animals, such as valuable domestic animals, and in laboratory animals, such as mice, rats and the like, responsive to treatment with central nervous system depressant agents. Specifically, the compounds may be employed to induce a calming effect in animals.

In the pharmacological evaluation of the biological activity of the compounds of this invention, the in vivo effects were tested by three different tests. In one, the oral toxicity was determined by administration to a group of laboratory mice. A trained observer watched the mice closely for several hours and noted decreased motor activity. The second test was the so-called "jiggle cage" method, a technique described by R. A. Turner, *Screening Methods in Pharmacology*, page 89, published 1965, Academic Press, New York, and summarized in Example 1. The third test was that described by Horn, *Biometrics*, 12:311 (1956). In this test, laboratory mice received the test compound (2 mice per dose level) at one-half log-dosage intervals by intravenous injection. The animals were observed by trained observers and pharmacological signs of tranquilization were noted. The median lethal dose ($LD_{50}$) and the median effective dose ($MED_{50}$) for tranquilization were estimated. The safety factor was taken as the ratio of $LD_{50}/MED_{50}$. The compounds of this invention are active as central nervous system depressants at a dose of about 0.01 to about 1000 mg/kg.

The invention will be better understood with reference to the following examples. It is understood, however, that the examples are intended for illustration only and it is not intended that the invention be limited thereby.

EXAMPLE 1

4,4-Dimethyl-2-(2-p-methoxyphenylethenyl)-2-oxazoline (P-1727) was synthesized by the method of H. L. Wehrmeister, *J. Org. Chem.* 27, 4418 (1962) from o-anisaldehyde and 2,4,4-trimethyl-2-oxazoline.

The product had a boiling point at 0.2–0.25 torr of 146°–151°; it analyzed 72.47% C, 7.86% H, 6.32% N, neutral equivalent 237.4. Calculated values are 72.69% C, 7.41% H, 6.06% N, and neutral equivalent 231.3.

Animals (rats) were tested for tranquilizer activity by the jiggle cage method of R. A. Turner, *Screening Methods in Pharmacology*, page 89, Academic Press, New York (1965). In this method, a cage is suspended from a rope and rests lightly on a pneumatic bed connected by a tube to a transducer. Activity in the cage results in changes of pressure on the pneumatic bed. The transducer changes these pressure variations to electrical impulses which are continuously recorded on a chart, making it possible to quantitate the amount, severity and frequency of the movement. The rats were fasted for 48 hours prior to testing to insure a high level of activity in the test cage.

At the time of the test, each rat was weighed and placed in the jiggle cage. All activity of the rat was measured by the pneumatic sensor. The rat was then removed from the cage and dosed with either a test material, negative control material, or standard material.

The rat was then placed in its original cage for 30 minutes. Following this, the rat was returned to the jiggle cage for ten minutes and all activity recorded. The test, control, and standard material were given to the rats via stomach tube.

The above compound (P-1727) was tested on three rats using the above time schedule, with each run a standard, chlordiazepoxide hydrochloride, and negative control test were performed on at least one rat. Both the standard and the test compound were administered as a suspension in water with 1% tragacanth. The negative control was 1% tragacanth in water.

The standard and all test substances were administered by stomach tube at a dosage level of 1 mg per 100 grams of body weight. The results obtained are as follows:

ACTIVITY DATA

| Rat No. | Condition | Σ of Evaluation Scores (ΣS) | Average Activity Value ΣS÷600 |
|---|---|---|---|
| 1 | Control (neg.) | 712* | 1.19 |
|   | Standard | 52* | .09 |
| 2 | Control (neg.) | 724 | 1.21 |
|   | Test 1 | 35 | .06 |
| 3 | Control (neg.) | 679 | 1.13 |
|   | Test 2 | 94 | .16 |
| 4 | Control (neg.) | 1670 | 2.78 |
|   | Test 3 | 54 | .09 |
| 5 | Control (neg.) | 1289 | 2.15 |
|   | Control (post.) | 425 | .71 |

*Average of 3 daily negative controls and standards.

ACTIVITY RESULTS

| No. of Animals | Condition | Corrected* Activity | Activity** Coefficient |
|---|---|---|---|
| 3 | Standard | 0.076 | 0.254 |
| 3 | Test | 0.058 | 0.272 |
| 1 | Positive Control | 0.330 | — |

*Activity After Material Dose

Activity Before Material Dose

**Corrected Activity Positive Control minus Corrected

ACTIVITY RESULTS-continued

| No. of Animals | Condition | Corrected* Activity | Activity** Coefficient |
|---|---|---|---|

Activity Condition.

The higher the score, the more tranquilizing activity exhibited by the materials.

The results show that P-1727 is about equal in activity to the standard.

EXAMPLE 2

2-(2-p-Chlorophenylethenyl)-4,4-dimethyl-2-oxazoline (P-1581) was synthesized from 2,4,4-trimethyl-2-oxazoline and p-chlorobenzaldehyde.

The acute $LD_{50}$ by oral administration to mice was determined to be $2725 \pm 340$ mg/kg. The $LD_0$ was 1500 mg/kg and the $LD_{100}$ was approximately 5400 mg/kg. Animals receiving the compound were observed to be tranquilized.

The compound was tested by the method of Horn, described above. It was dissolved in polyethylene glycol 300 and was administered intravenously at dosage levels of 10, 32, 100 and 320 mg/kg to mice, two animals per dosage level. The dilution was such that each animal received a dose of 1 ml of solution per kilogram of body weight. A trained observer watched the animals for evidence of central nervous system depressant activity in general and tranquilizing activity in particular. The dosage at which these signs became apparent was reported as the median effective dose ($MED_{50}$) and the safety factor, the ratio $LD_{50}/MED_{50}$, was determined. The $LD_{50}$ was determined to be 180 mg/kg (range 56–560 mg/kg). The median effective dose was 18 mg/kg (range 5.6–56) and the safety factor was 10.0.

EXAMPLE 3

2-(2-m-Chlorophenylethenyl)-4,4-dimethyl-2-oxazoline (P-1895) was prepared by reacting m-chlorobenzaldehyde with 2,4,4-trimethyl-2-oxazoline.

The acute $LD_{50}$ by oral administration to mice was determined to be $1080 \pm 166$ mg/kg. The $LD_0$ was >990 mg/kg and the $LD_{100}$ was <1600 mg/kg. Animals receiving the compound were strongly tranquilized.

The compound was tested by the method of Horn as described in Example 2. The $LD_{50}$ was 100 mg/kg (range 32–320) and the median effective dose for tranquilization was 18 (range 5.6–56). The safety factor was 5.6.

EXAMPLE 4

3,5-Dimethoxybenzaldehyde was reacted with 2,4,4-triethyl-2-oxazoline to produce 2-[2-(3,5-dimethoxyphenyl)-1-methylethenyl]-4,4-dimethyl-2-oxazoline (P-1641), b.p. 171°–173° at 0.25 mm. It was administered to mice to determine the acute oral toxicity and a trained observer studied the animals for tranquilizing activity. The oral $LD_0$ was determined to be over 5 g/kg and the animals receiving it were observed to be highly tranquilized. The compound is administered orally to animals in need of tranquilizing in a dosage of from about 100 to about 1000 mg/kg.

EXAMPLE 5

The experiment of Example 2 was repeated in all essential details except that 2,4,4-trimethyl-2-oxazoline was substituted for 2-ethyl-4,4-dimethyl-2-oxazoline.

The product obtained was 2-(2-o-chlorophenylethenyl)-4,4-dimethyl-2-oxazoline (P-1888), b.p. 141 (0.48 mm)–148 (0.65 mm). The $LD_{50}$ by oral administration was determined to be 2800 ± 305 mg/kg. The $LD_0$ was 1500 mg/kg and the $LD_{100}$ was 4000 mg/kg. Animals receiving it were tranquilized. At the toxic dose levels the compound caused convulsions. The compound is administered orally to animals in need of tranquilizing in a dosage of from about 56 to about 560 mg/kg.

EXAMPLE 6

4,4-Dimethyl-2-[2-(2-thienyl)ethenyl]-2-oxazoline (P-1894) was synthesized by reacting 2-thiophenecarboxaldehyde with 2,4,4-trimethyl-2-oxazoline.

The acute $LD_{50}$ in mice by oral administration was 1900 ± 100 mg/kg. The $LD_0$ was 1650 and the $LD_{100}$ was 2800 mg/kg. Animals receiving the compound were tranquilized.

The compound was tested by the method of Horn described in Example 2. The $LD_{50}$ by intravenous administration was 180 mg/kg (56–560) and the median effective dose for tranquilization was 18 mg/kg (5.6–56) and the safety factor was 10.

EXAMPLE 7

3,4,5-Trimethoxybenzaldehyde was reacted with 2,4-4-trimethyl-2-oxazoline as described in Example 1 to produce 4,4-dimethyl-2-[2-(3,4,5-trimethoxyphenyl)ethenyl]-2-oxazoline (P-1730), m.p. 116–118.

The acture oral toxicity was determined by administration to mice. The $LD_{50}$ was 1400 ± 233. The $LD_0$ was 350 and the $LD_{100}$ was 2600. Animals receiving the product were observed to be tranquilized.

The compound was tested by the method of Horn. The $LD_{50}$ by intravenous administration was 180 (56–560) mg/kg. The median effective dose for tranquilization was 10 (3.2–32.0) and the safety factor was 18.0.

EXAMPLE 8

4,4-Dimethyl-2-(2-p-methoxyphenyl-1-methylethenyl)-2-oxazoline (P-1642) was synthesized from o-anisaldehyde and 2-ethyl-4,4-dimethyl-2-oxazoline. The product distilled at 151°–164°C at a pressure of 0.2–0.25 torr. It analyzed 73.01% C, 7.96% H, 6.12% N, neutral equivalent 243.3. Calculated values were 73.44% C, 7.81% H, 5.71% N, neutral equivalent 245.3.

The acute oral toxicity was determined by administration to mice. The $LD_{50}$ was 2500 ±550 mg/kg. The $LD_0$ was 800 and $LD_{100}$ was 6700 mg/kg. Animals receiving the compound were tranquilized.

The compound was additionally tested by the method of Example 1 except that P-1642 was substituted for P-1727. The results, which are as follows, show that P-1642 is about as active a tranquilizer as the standard.

ACTIVITY DATA

| Rat No. | Condition | Σ of Evaluation Scores (ΣS) | Average Activity Value ΣS÷600 |
|---|---|---|---|
| 1 | Control (neg.) | 613 | 1.02 |
|   | Standard | 20 | .03 |
| 2 | Control (neg.) | 171* | .28 |
|   | Test 1 | 70 | .12 |
| 3 | Control (neg.) | 511 | .85 |

ACTIVITY DATA-continued

| Rat No. | Condition | Σ of Evaluation Scores (ΣS) | Average Activity Value ΣS÷600 |
|---|---|---|---|
|   | Test 2 | 4 | .01 |
| 4 | Control (neg.) | 624 | 1.04 |
|   | Test 3 | 41 | .07 |
| 5 | Control (neg.) | 1289 | 2.15 |
|   | Control (post.) | 425 | .71 |

*This data rejected and not used in further calculations of activity on the basis of the relative inactivity of the rat under conditions of control.

ACTIVITY RESULTS

| No. of Animals | Condition | Corrected* Activity | Activity** Coefficient |
|---|---|---|---|
| 1 | Standard | 0.029 | 0.301 |
| 2 | Test | 0.036 | 0.294 |
| 1 | Positive Control | 0.330 | — |

*Activity After Material Dose
Activity Before Material Dose

**Corrected Activity Positive Control minus Corrected Activity Condition.

The higher the score, the more tranquilizing activity exhibited by the material.

EXAMPLE 9 p-Chlorobenzaldehyde was reacted with 4,4-dimethyl-2-phenylmethyl-2-oxazoline in about equimolar quantities.

There was obtained 2-(2-p-chlorophenyl)-1-phenylethenyl)-4,4-dimethyl-2-oxazoline (P-1884). Two isomers were obtained, one melting at 138°–140°, the other at 89°–91°. The nmr spectrum of the high-melting isomer and the infrared absorption spectra for both isomers were consistent with the proposed structures.

The high-melting isomer was tested by the method of Horn. The $LD_{50}$ by intravenous administration was 180 mg/kg (56–560.0). The median effective dose for tranquilization was 18 mg/kg (5.6–56.0) and the safety factor was 10. Animals receiving the compound were tranquilized.

EXAMPLE 10

4,4-Dimethyl-2-(2-phenylethenyl)-2-oxazoline (P-1886) was prepared by reacting benzaldehyde with 2,4,4,-trimethyl-2-oxazoline. The product had a boiling point of 112° at 0.45mm. The nmr spectrum was consistent with the proposed structure.

The compound was tested by the method of Horn. The $LD_{50}$ by intravenous administration was 180 mg/kg (56.0–560.0 mg/kg). The median effective dose for tranquilization was 5.6 mg/kg (1.8–18.0) and the safety factor was 32.0.

EXAMPLE 11

3-Methoxybenzaldehyde was reacted with 4,4-dimethyl-2-ethyl-2-oxazoline by the method of Example 1 to produce 2-[2-(3-methoxyphenyl)-1-methylethenyl]-4,4-dimethyl-2-oxazoline (P-1643), b.p. 138 at 0.1 mm to 150 at 0.25 mm. The $LD_0$ by oral administration to mice was over 5.0 g/kg. The $LD_{50}$ was not determined. Animals receiving the compound were tranquilized. The compound is administered orally to animals in need of tranquilizing in a dose of from about 100 to about 1000 mg/kg.

EXAMPLE 12

4,4-Dimethyl-2(2-α-furylethenyl)-2-oxazoline (P-1906) was prepared by reacting furfural with 2,4,4-trimethyl-2-oxazoline. The product had a boiling point of 87° at 0.14 mm and the nmr spectrum and infra-red absorption spectrum were consistent with the proposed structure. The oral $LD_0$ by adminstration to mice was 50 mg/kg; the $LD_{50}$ was 212 and the $LD_{100}$ was 300 mg/kg.

The compound was tested by the method of Horn. The $LD_{50}$ by intravenous administration was 32 mg/kg (10.0–100.0). The median effective dose for tranquilization was 3.2 mg/kg and the safety factor was 10.0.

EXAMPLE 13

Benzaldehyde was reacted with 4,4-dimethyl-2-methoxymethyl-2-oxazoline (derived from methoxyacetic acid) to produce 2-(2-phenyl-1-methoxyethenyl)-4,4-dimethyl-2-oxazoline (P-1907), b.p. 122 (0.3 mm)–125 (0.26 mm).

The $LD_{50}$ by oral administration to mice was 2.8 g/kg. The $LD_0$ was 1500 mg/kg and the $LD_{100}$ was 4500 mg/kg. Animals receiving it were strongly tranquilized.

The compound was tested by the method of Horn. The $LD_{50}$ by intravenous administration was 100 mg/kg (32–320.0) and the median effective dose for tranquilization was 18.0 mg/kg (5.6–56.0). The safety factor was 5.6.

EXAMPLE 14

3,5-Dimethoxybenzaldehyde was reacted with 4,4-dimethyl-2-(9-decenyl)-2-oxazoline (P-1729) by the method of Example 1 to produce 2-[2-(3,5-dimethoxyphenyl)-1-(8-nonenyl)-ethenyl]-4,4-dimethyl-2-oxazoline (P-1729), b.p. 214 (0.4 mm)–217 (0.3 mm); 202–212 (0.2 mm). It was administered to mice to determine the oral toxicity. The $LD_0$ was greater than 5 g/kg. Animals receiving the product were observed to be mildly tranquilized. The compound is administered orally to animals in need of tranquilizing in a dosage of from about 100 to about 1000 mg/kg.

EXAMPLE 15

4,4-Dimethyl-2-(p-methoxybenzyl)-2-oxazoline (P-1866) was prepared by reacting p-methoxyphenylacetic acid with 2-amino-2-methyl-1-propanol according to the methods known in the art, e.g., R. F. Purcell, U.S. Pat. No. 3,336,145.

The acute oral toxicity was determined by administration to mice. The $LD_{50}$ was 1900 ± 465 mg/kg. The $LD_0$ was 400 and the $LD_{100}$ was 4000 mg/kg. Animals receiving the product were tranquilized.

The compound was additionally tested by the method of Example 1 except that P-1866 was substituted for P-1727.

The results obtained, which show that P-1866 is about twice as active a tranquilizer as the standard, are as follows:

ACTIVITY DATA

| Rat No. | Condition | Σ of Evaluation Scores (ΣS) | Average Activity Value ΣS÷600 |
|---|---|---|---|
| 1 | Control (neg.) | 702 | 1.17 |
|   | Standard | 142 | 0.24 |
| 2 | Control (neg.) | 1129 | 1.88 |
|   | Test 1 | 214 | 0.35 |
| 3 | Control (neg.) | 562 | 0.93 |
|   | Test 2 | 13 | .02 |
| 4 | Control (neg.) | 916 | 1.53 |
|   | Test 3 | 11 | .02 |
| 5 | Control (neg.) | 1289 | 2.15 |
|   | Control (post.) | 425 | 0.71 |

ACTIVITY RESULTS

| No. of Animals | Condition | Corrected* Activity | Activity** Coefficient |
|---|---|---|---|
| 1 | Standard | .205 | .125 |
| 3 | Test | .074 | .256 |
| 1 | Positive Control | 0.330 | — |

*Activity After Material Dose
Activity Before Material Dose

**Corrected Activity Positive Control − Corrected Activity Condition

The higher the score, the more tranquilizing activity exhibited.

EXAMPLE 15A

The foregoing experiment was repeated in all essential details except that a compound structurally similar to P-1866 was used. The compound was 4,4-dimethyl-2-(4-methoxyphenyl)-2-oxazoline. It had no tranquilizing activity.

The compound was also tested by the method of Horn. The $LD_{50}$ by intravenous administration was 180 (56–560.0). The median effective dose for tranquilization was 56 (18.0–180.0). The safety factor was 3.2.

EXAMPLE 16

(R,S)-4-Ethyl-2-(p-methoxybenzyl)-2-oxazoline (P-1891) was prepared by reacting 2-amino-1-butanol with p-methoxyphenylacetic acid.

The acute $LD_{50}$ by oral administration to mice was not determined, but the acute $LD_{70}$ was 5000 mg/kg. Animals receiving the compound were tranquilized.

The compound was additionally tested by the method of Horn. The $LD_{50}$ by intravenous administration was 180 (56.0–560.0) mg/kg and the median effective dose for tranquilization was 5.6 mg/kg (1.8–18.0). The safety factor was 32.0.

EXAMPLE 17

5,6-Dihydro-2-(p-methoxyphenylmethyl)-1,3-oxazine (P-1899), b.p. 117 at 0.22 mm, was prepared as follows:

4-Methoxyphenyl acetic acid, 49.8 g (0.3 mole), and 3-amino-1-propanol, 45.1 g (0.6 mole), were dissolved in 100 ml xylene. The mixture was heated with stirring at 140°–175°C at reflux, removing some xylene toward end. The product was probably the amide at this point. The remaining xylene was removed by distillation and the residue was distilled at 0.4 mm, at 140°–160°C. The distillate was redistilled and dissolved in benzene; it was washed with 10% $NaHCO_3$ solution, then redistilled at 104° (0.15 mm)–121° (0.24 mm). The distillate was dissolved in 100 ml of benzene and extracted twice with 50 ml portions of 3N HCl. The extract was made alkaline with Na$_2$CO$_3$ and extracted with a mixture of benzene and chloroform. The extract was dried, filtered and the solvent was stripped by distillation. The product was then distilled at 117° (0.2 mm).

The acute oral LD$_{50}$ by administration to mice was 3400 mg/kg. The LD$_0$ was 2400 mg/kg and the LD$_{100}$ was 4800 mg/kg. Animals receiving the compound were tranquilized.

The compound was additionally tested by the method of Horn. The LD$_{50}$ by intravenous administration was 56.0 (18.0–180.0) mg/kg, and the median effective dose for tranquilization was 5.6 mg/kg (1.8–18.0). The safety ratio was 10.0.

EXAMPLE 18

2-Benzyl-4,4-dimethyl-2-oxazoline (P-1890), b.p. 83–86 at 1.0 mm, was made from phenylacetic acid and 2-amino-2-methyl-1-propanol by the method of Example 15. The acute oral LD$_{50}$ by administration to mice was 1400 mg/kg. The LD$_0$ was 600 mg/kg and the LD$_{100}$ was 2400 mg/kg. The animals receiving it were tranquilized.

The product was additionally tested by the method of Horn. The LD$_{50}$ by intravenous administration was 180.0 (56.0–560.0) mg/kg and the median effective dose for tranquilization was 3.2 mg/kg (1.0–10.0). The safety factor was 56.0.

EXAMPLE 19

2-(2-Dichlorophenoxymethyl)-4,4-dimethyl-2-oxazoline (P-1902) was prepared by reacting 2,4-dichlorophenoxyacetic acid with 2-amino-2-methyl-1-propanol.

The acute LD$_{50}$ by oral administration to mice was determined to be 925 ± 170 mg/kg. The LD$_0$ was 500 and the LD$_{100}$ was approximately 1800 mg/kg. Animals receiving the compound were tranquilized.

The compound was further tested by the method of Horn. The LD$_{50}$ by intravenous administration was 180.0 (56.0–560.0) mg/kg. The median effective dose for tranquilization was 32.0 mg/kg (10.0–100.0) and the safety factor was 5.6.

EXAMPLE 20

4,4-Dimethyl-2-(2-p-methoxyphenylethyl)-2-oxazoline (P-1882) was prepared from p-methoxyphenylpropionic acid and 2-amino-2-methyl-1-propanol.

The oral LD$_{50}$ by administration to mice was 2800 ± 110 mg/kg. The LD$_0$ was 2400 mg/kg and the LD$_{100}$ was 5600 mg/kg. Animals receiving the compound were tranquilized. The compound was tested by the method of Horn. The LD$_{50}$ by intravenous administration was 180.0 (56.0–560.0) mg/kg, and the median effective dose for tranquilization was 18 mg/kg (5.6–56.0). The safety factor was 10.0.

EXAMPLE 21

2-[1,2-Bis(4-methoxyphenyl)ethenyl]-4,4-dimethyl-2-oxazoline (P-1728) was prepared by reacting 4-methoxyphenyl acetic acid with 2-amino-2-methyl-1-propanol and condensing the product thereby obtained with p-methoxybenzaldehyde. The boiling point was about 223 at 0.38 mm. The nmr spectrum was consistent with the proposed structure.

The oral LD$_{50}$ by administration to mice was higher than 5.0 g/kg. The LD$_0$ was near 5.0 g/kg. Animals receiving the compound were mildly tranquilized.

The compound was tested by the method of Horn. The LD$_{50}$ by intravenous administration was greater than 320.0 mg/kg. The median effective dose for tranquilization was 5.6 mg/kg (1.8–18.0) and the safety factor was greater than 56.

EXAMPLE 22

The experiment of Example 9 was repeated in all essential details except that 3,5-dimethoxybenzaldehyde was substituted for p-chlorobenzaldehyde. There was obtained 2-[2-(3,5-dimethoxyphenyl)-1-phenylethenyl]-4,4-dimethyl-2-oxazoline (P-1644), b.p. 206°–208° at 0.25 mm. The nuclear magnetic resonance spectrum and the infra-red absorption spectrum were consistent with the proposed structure.

The compound was tested by oral administration to mice. The LD$_{50}$ was 1525 ± 350 mg/kg. The LD$_0$ was 800 and the LD$_{100}$ was 3275 mg/kg. Animals receiving the compound were tranquilized.

The compounds of this invention are weakly alkaline and readily form salts with most acids. Many of these salts are water-soluble and advantageously can be used for administering these compounds. The invention therefore contemplates the administration of pharmaceutically acceptable salts of the disclosed compounds as well as the unneutralized compounds themselves.

We claim:

1. A compound represented by the formula

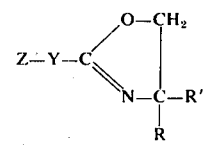

wherein Z is meta or para-methoxyphenyl; Y is —CH$_2$—,

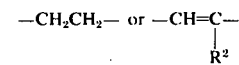

with the proviso that the CR$^2$ moiety is bonded to the oxazoline ring, where R$^2$ is hydrogen, methyl or 4-methoxypheny; R and R' are methyl except that when Y is —CH$_2$—, R and R' are methyl or R is hydrogen and R' is ethyl.

2. A compound represented by the formula

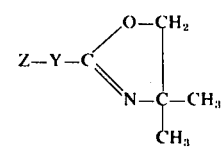

wherein Z is 3,5-dimethoxyphenyl, and Y is

with the proviso that the CR$^2$ moiety is bonded to the oxazoline ring and R$^2$ is methyl, nonenyl or phenyl.

3. A compound represented by the formula
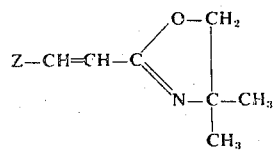
where Z is thienyl, furyl or 3,4,5-trimethoxyphenyl.
4. A compound of claim 3 where Z is 2-furyl.
5. A compound of claim 3 wherein Z is 2-thienyl and Y is —CH=CH—.
6. A compound of claim 3 wherein Z is trimethoxyphenyl.
7. 5,6-Dihydro-2-(p-methoxyphenylmethyl)-1,3-oxazine.
8. 2-(2-Phenyl-1-methoxyethenyl)-4,4-dimethyl-2-oxazoline.
* * * * *

UNITED STATES PATENT OFFICE
CERTIFICATE OF CORRECTION

Patent No. 3,953,432   Dated April 27, 1976

Inventor(s) Herbert L. Wehrmeister

It is certified that error appears in the above-identified patent and that said Letters Patent are hereby corrected as shown below:

Column 2, lines 2 and 3, "-CH=λCH-" should read -- -CH=CH- --

Column 2, line 21, "appopriate" should read -- appropriate --

Column 4, line 44, "990 mg/kg" should read -- 900 mg/kg --

Column 10, line 23, "wealky" should read -- weakly --

Column 10, claim 1, line 50, "4-methoxypheny" should read -- 4-methoxyphenyl --

Signed and Sealed this ninth Day of August 1977

[SEAL]

Attest:

RUTH C. MASON
Attesting Officer

C. MARSHALL DANN
Commissioner of Patents and Trademarks